United States Patent [19]

Tanner

[11] Patent Number: 4,526,170
[45] Date of Patent: Jul. 2, 1985

[54] DETACHABLE LASER OPTICAL FIBER ASSEMBLY AND METHOD OF ADJUSTMENT

[75] Inventor: Howard M. C. Tanner, Salt Lake City, Utah

[73] Assignee: HGM, Inc., Salt Lake City, Utah

[21] Appl. No.: 478,158

[22] Filed: Mar. 23, 1983

[51] Int. Cl.³ .......................................... A61B 17/36
[52] U.S. Cl. .................... 128/303.1; 128/398
[58] Field of Search ................................. 128/4–8,
128/303.1, 395–398; 350/96.15, 96.2–96.26;
362/32, 289

[56] References Cited

U.S. PATENT DOCUMENTS

| | | | |
|---|---|---|---|
| 3,538,919 | 11/1970 | Meyer | 128/398 |
| 3,692,415 | 9/1972 | Shiller | 350/96.24 |
| 3,699,950 | 10/1972 | Humphrey et al. | 350/96.23 |
| 3,769,963 | 11/1973 | Goldman et al. | 128/303.1 |
| 4,186,999 | 2/1980 | Harwood et al. | 350/96.21 |
| 4,193,664 | 3/1980 | Ellwood | 350/96.21 |
| 4,261,640 | 4/1981 | Stankos et al. | 350/96.15 |
| 4,325,606 | 4/1982 | Ikuno et al. | 350/96.2 |
| 4,351,586 | 9/1982 | Phillips et al. | 350/96.2 |
| 4,388,924 | 6/1983 | Weissman et al. | 128/398 |
| 4,421,382 | 12/1983 | Doi et al. | 128/303.1 |

FOREIGN PATENT DOCUMENTS

| | | | |
|---|---|---|---|
| 2740969 | 3/1979 | Fed. Rep. of Germany | 128/395 |
| 2828322 | 1/1980 | Fed. Rep. of Germany | 128/303.1 |
| 2644104 | 10/1980 | United Kingdom | 128/398 |

Primary Examiner—Edward M. Coven
Assistant Examiner—Max F. Hindenburg
Attorney, Agent, or Firm—B. B. Olive

[57] ABSTRACT

A detachable optical fiber assembly for transmitting a laser beam from a laser source to a surgical laser instrument such as a slit lamp or operating microscope. The assembly comprises an optical fiber enclosed within a protective casing with connectors attached to the ends thereof. The connector which attaches the fiber to the laser source includes means for adjusting the alignment of the fiber within the connector as well as the depth to which it penetrates the socket in the laser source to insure that the tip of the fiber is positioned at the focal point of the laser beam.

1 Claim, 4 Drawing Figures

DETACHABLE LASER OPTICAL FIBER ASSEMBLY AND METHOD OF ADJUSTMENT

BACKGROUND

1. Field of the Invention

The present invention relates to optical fiber assemblies used to connect surgical laser instruments to a laser source and, more particularly, to an adjustable, detachable optical fiber assembly which can be used to connect a surgical instrument such as a slit lamp or operating microscope to a laser source.

2. The Prior Art

The advent of the laser has greatly expanded the frontiers of many areas of science. One of the most significant applications of this new laser technology has been in the field of medicine. Lasers possess many features which make them uniquely adaptable to various types of surgical procedures.

For purposes of surgery, lasers operate on the principle that the highly collimated laser light beam may be converted into thermal energy when focused on a particular point on living tissue. This heat can be used to create incisions, coagulate blood, destroy diseased cells and perform many other functions.

Different types of lasers affect different types of tissues in various ways. For example, the wave length of light produced by a carbon dioxide laser is readily absorbed by water and other body fluids. On the other hand, the light produced by an argon laser readily passes through clear fluids and tissue but is absorbed by pigmented tissue and by colored fluids such as blood.

The ability of the argon laser to pass through transparent fluids and tissue has made it especially suitable for use in various types of ophthalmic surgery. For example, in 1965 doctors first utilized an argon laser to repair a detached retina. The surgeons were able to focus the laser into the interior portion of the eyeball and "weld" the detached retina back into place. At the point where the laser beam struck the retina, the light energy was converted into heat energy which produced a coagulum. During the next few weeks, this coagulum was converted to scar tissue which anchored the retina in place.

Since that time, this procedure has been much improved and the utilization of lasers has become a generally accepted method of repair of this type of abnormality. Surgical laser apparatus has also been used to repair retinal tears and abnormal blood vessels within the eye.

When using a laser to perform ophthalmic surgery, the surgeon often utilizes an instrument which is generally referred to as an operating microscope. The operating microscope is typically mounted above the operating table and is connected to a laser source by means of a flexible optical fiber. Through the operating microscope, the surgeon can obtain a magnified view of the area upon which he needs to perform the surgical operation. The surgeon can then activate the laser source by means of a foot switch and the laser light transmitted through the optical fiber is focused through a series of lenses in the operating microscope onto the point at which the laser needs to be applied.

Many operations have become routine enough that an ophthalmologist can now perform them in his office utilizing what is commonly referred to as a "slit lamp." This device, like an operating microscope, is connected to a laser source by means of a flexible optical fiber. The slit lamp also utilizes a series of lenses to focus the laser beam onto the point at which the surgical operation needs to be performed.

Notwithstanding the substantial advances in ophthalmic surgery which have come about as a result of the use of laser technology, the current state of the art leaves much to be desired. One of the primary concerns faced by doctors and hospitals is the extremely high cost of laser equipment. The laser source, slit lamp and operating microscope are all extremely expensive.

One of the problems which has hindered the use of laser systems and which adds to their cost has been the breakdown of the optical fiber which connects the slit lamp or operating microscope to the laser source. The optical fiber is extremely thin, generally being on the order of about 100 microns in diameter, and is extremely fragile. Accordingly, the fiber is usually encased within a silicone sheath and is then placed within some type of casing for additional protection. Nevertheless, even with the utmost care, a certain amount of degradation of the optical fiber occurs with time. The optical fiber is also subject to accidental breakage and the ends of the fiber can become dirty, thus interfering with the transmission of the laser beam.

Because of the extremely small diameter of the optical fiber, it is important that the laser beam be focused directly onto the tip of the fiber. If the laser beam is not properly aligned with the end of the optical fiber, much of its power can be lost. Additionally, the misdirected beam can vaporize portions of the connector, thus destroying it or creating debris which can obscure the end of the fiber, which also reduces the amount of light which can be transmitted. Accordingly, in the past it has been customary to permanently attach the optical fiber to the laser source in order to achieve and maintain proper alignment of the fiber with the laser output.

In the prior art devices, because the optical fiber is permanently attached to the laser source, if any type of fiber breakdown occurs, the whole unit has to be sent back to the factory for repair. This creates added expense to the maintenance of the laser system and also causes inconvenience. Because it may take a substantial amount of time to have the optical fiber replaced, scheduled operations have to be cancelled and emergency operations cannot be performed unless a back-up laser system is maintained. However, because of the high cost of the laser system, it is extremely expensive and thus often impractical to have a back-up system.

Accordingly, what is needed in the art is a fiber assembly which can be used with slit lamps and the like and which is detachable from both the slit lamp and the laser source for easy replacement or repair. The fiber assembly must also be capable of providing the extremely fine alignment necessary to insure that the laser beam is accurately focused onto the end of the optical fiber.

OBJECTS AND BRIEF SUMMARY OF THE INVENTION

It is a primary object of the present invention to provide a novel fiber assembly which is detachable from both a surgical instrument such as a slit lamp and from a laser source.

It is a further object of this invention to provide a detachable fiber assembly which has an adjustable connector for attaching the assembly to a laser source such that the optical fiber can easily be accurately aligned with the output beam of the laser source.

Another object of this invention is to provide a fiber assembly which can be detached from a laser source without disturbing any previously made adjustments for aligning the optical fiber with the output beam of the laser source.

Yet another object of the present invention is to provide a method for easily and accurately aligning a detachable fiber assembly with the output of a laser source.

These and other objects and features of the present invention will become more fully apparent from the following description and appended claims taken in conjunction with the accompanying drawings.

In accordance with the foregoing objects, the present invention provides a novel fiber assembly which is detachable from both a surgical instrument such as a slit lamp and from a laser source. The connector which attaches the fiber assembly to the laser source is designed such that the vertical and horizontal position of the fiber can be adjusted as well as the depth to which it is inserted into the laser source so that the optical fiber can be precisely aligned with the focused laser beam output of the laser source. Additionally, the connector is designed such that it will maintain these focused adjustments when the fiber assembly is disconnected and subsequently reattached to the laser source.

In the presently preferred embodiment, the detachable fiber assembly of the present invention comprises a silicone-clad quartz fiber which optically transmits the laser beam from the laser source to a slit lamp or operating microscope. The fiber is enclosed within a plastic casing which has connectors fastened to both ends for detachably connecting the fiber to the laser source and a surgical instrument such as a slit lamp.

The proximal connector, which attaches the fiber to the laser source, is designed to hold the fiber such that its tip can be precisely aligned with the focused laser beam output of the laser source. In the preferred embodiment, the proximal connector includes two concentric sleeves which are placed over the end of the fiber. These sleeves are positioned within a plug which is designed to engage a corresponding socket located in the laser source. One end of the concentric sleeves is securely anchored within the plug and the other end is supported by a series of four set screws. The screws are used to horizontally and vertically adjust the concentric sleeves, thereby aligning the tip of the optical fiber.

The proximal connector also includes an adjustable collar surrounding the plug to regulate the depth to which the plug and thus the optical fiber, can be inserted into the output socket of the laser source. Accordingly, the position of the tip of the optical fiber can be adjusted in three dimensions within the output socket.

A cap is placed over the connector to securely retain and protect the concentric sleeves, the set screws and the collar once the alignment of the optical fiber is completed.

A distal connector is connected to the opposite end of the casing and optical fiber for attaching the optical fiber to a slit lamp or similar instrument. The distal connector includes a plug which fits in a corresponding inlet socket located in the slit lamp. The distal tip of the optical fiber is mounted within the plug, and a cap covers the proximal end of the plug and secures the connector to the casing surrounding the optical fiber.

The entire fiber assembly is designed such that it can easily be detached from the laser source and the slit lamp for replacement or repair. Additionally, the proximal connector is designed such that once the optical fiber has been aligned to coincide with the focused laser beam, it will retain its alignment during subsequent detachment and reconnection.

BRIEF DESCRIPTION OF THE DRAWINGS

Reference is next made to the drawings, in which like parts are designated with like numerals throughout and in which.

DETAILED DESCRIPTION OF THE PREFERRED EMBODIMENT

Figure 1:
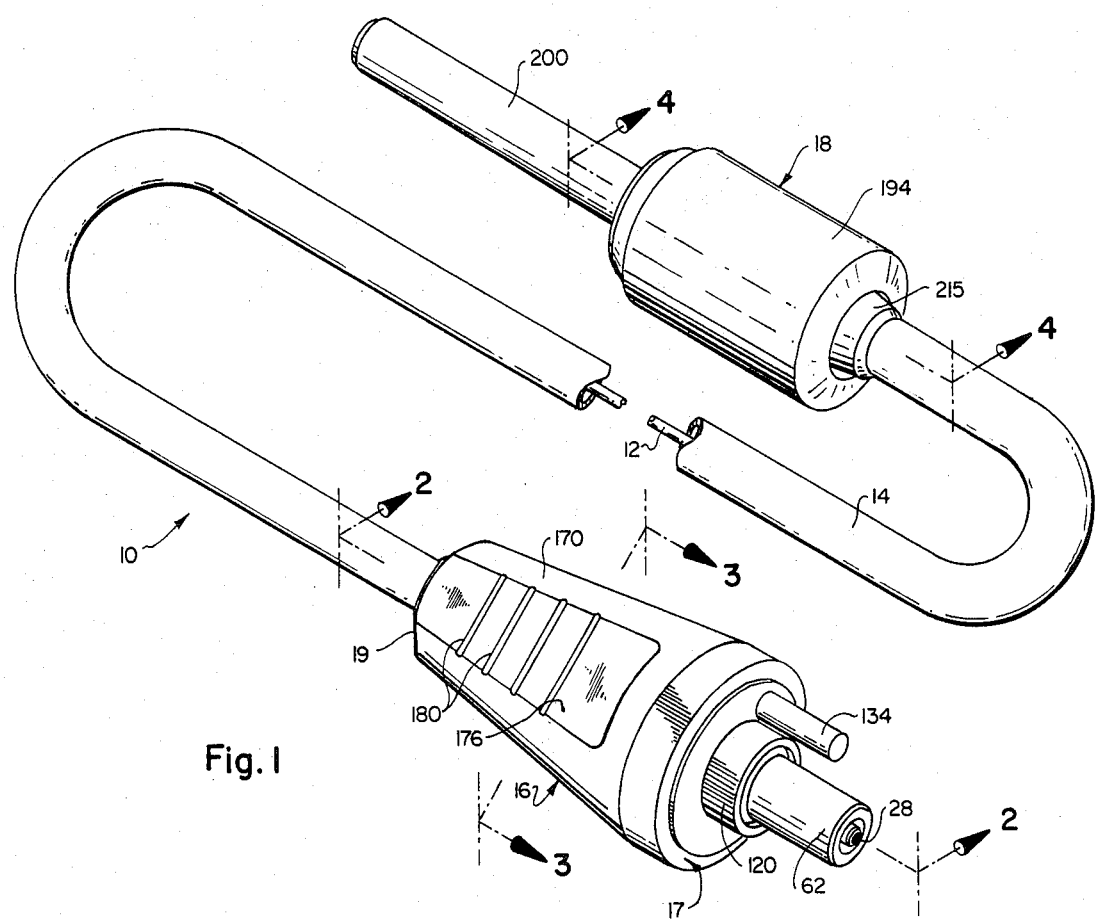
FIG. 1 is a perspective view of the optical fiber, casing and connectors forming the detachable fiber assembly of the present invention.

Referring first to FIG. 1, the detachable fiber assembly of the present invention is generally designated at 10. The apparatus includes an optical fiber 12 which is enclosed within a protective casing 14. In the preferred embodiment, optical fiber 12 may be, for example, a 100 micron quartz fiber which is covered by a thin layer of silicone cladding which enhances the optical transmission properties of the quartz fiber and also forms a protective sheath to protect the quartz fiber from damage. Casing 14 which surrounds fiber 12 is formed from plastic or other suitable material and is designed to provide additional protection for fiber 12.

A proximal connector generally designated at 16 is connected to one end of the optical fiber 12 and casing 14 for attaching the assembly to a laser source, as hereinafter more fully described. A distal connector which is generally designated at 18 is connected to the opposite end of the optical fiber 12 and casing 14 for attaching the assembly to a slit lamp, operating microscope, or other such surgical instrument.

When attaching the fiber assembly 10 to a laser source, it is of utmost importance to insure that the proximal end 28 of the optical fiber 12 is precisely aligned with the focused laser beam generated at the output of the laser source. Accordingly, as will be more fully discussed hereinafter connector 16 is designed such that the position of the end 28 of fiber 12 can be adjusted within connector 16 so that it can be very precisely aligned with the laser beam output by the laser source.

With continued reference to FIG. 1, connector 16 includes an outer cap 170 which protects the alignment mechanisms located in the interior of connector 16. Projecting from the proximal end of connector 16 which is generally designated 17, is a portion of a plug 62 which is inserted into a corresponding socket formed in a laser source. Optical fiber 12 passes through plug 62 and the proximal end 28 of fiber 12 extends almost to the end of the plug. Thus, when plug 62 is securely inserted into the socket of the laser source, the position of end 28 within plug 62 determines whether or not the fiber is in alignment.

The depth to which plug 62 penetrates the socket is determined by an adjustable collar 120 which surrounds plug 62. When plug 62 of connector 16 is inserted into the socket of the laser source, collar 120 abuts against the face of the socket to limit the penetration of plug 62. A difference of only a fraction of a millimeter may determine whether or not the end 28 of fiber 12 is correctly positioned at the focal point of the laser beam. Thus, as more fully discussed hereinafter, collar 120 can be longitudinally adjusted along the length of plug 62 to insure that the end 28 of fiber 12 is properly positioned at the focal point.

When reinserting plug 62 into the socket of the laser source after removal, it is important that the plug not be rotated from its previously aligned position as this could shift the end 28 of fiber 12 out of alignment. To insure consistent positioning, pin 134 is set in collar 120. Pin 134 mates with a corresponding bore (see FIG. 2) formed in the laser source immediately above the socket into which plug 62 is inserted. Thus, there is only one position at which plug 62 can be inserted. Pin 134 also prevents plug 62 from being rotated once it has been inserted.

Cap 170 which covers connector 16 is generally conical in shape being tapered from its proximal end 17 to its distal end 19. The sides of cap 170 are cut away as at 176 and 178 (see also FIG. 3) to form generally planar surfaces. These planar surfaces 176 and 178 provide a convenient gripping surface for inserting or removing connector 16. Grooves 180 are formed in planar surfaces 176 and 178 to enhance the gripping surface.

With continued reference to FIG. 1, the distal connector 18 is utilized to attach the other end of optical fiber 12 to a slit lamp or operating microscope (not shown). Inasmuch as the laser light exiting from fiber 12 is typically focused through a series of lenses in the slit lamp or operating microscope, the positioning of the tip of the optical fiber is not as critical as it is with connector 16. Nevertheless, it is important that connector 18 provide a secure means for connecting the fiber to the surgical instrument, and that it also provide some protection to fiber 12.

In the preferred embodiment as illustrated in FIG. 1, connector 18 comprises a cylindrical cap 194 and a generally cylindrical plug 200. Plug 200 is designed to be detachably inserted into a socket formed in a surgical instrument such as a slit lamp or operating microscope. Cap 194 connects plug 200 with casing 14 and provides a means for grasping connector 18 for insertion or removal.

Figure 2:
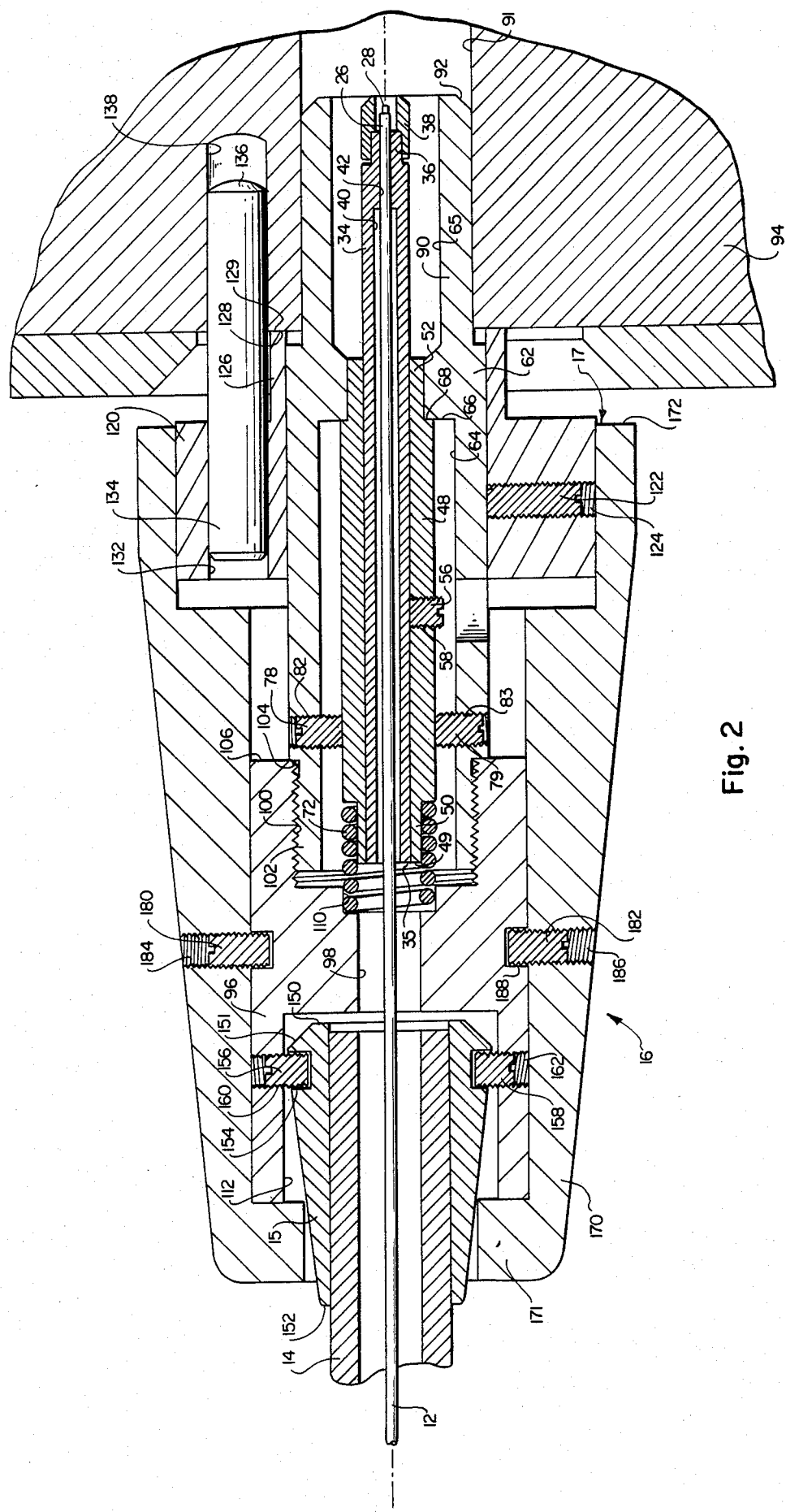
FIG. 2 is an enlarged cross-sectional view of the proximal connector taken along line 2—2 of FIG. 1.

Reference is next made to the enlarged cross-sectional view of FIG. 2, which illustrates the proximal connector 16 in greater detail.

Optical fiber 12 extends axially through the center of connector 16 and the proximal end 28 of fiber 12 is anchored within an inner sheath 34 by bonding or other suitable means. Sheath 34 is a generally cylindrical tube which in the preferred embodiment is machined from brass and which, by way of example, is approximately 1½ inches long and approximately ⅛ inch in diameter. Sheath 34 has a bore 40 running through the length thereof through which fiber 12 passes. The greater portion of bore 40 has a diameter which is larger than the diameter of optical fiber 12 which facilitates insertion of fiber 12 through sheath 34 during assembly. At its proximal end, bore 40 also has a radially reduced portion 42 into which fiber 12 is securely bonded, and which is designed to anchor optical fiber 12 so as to prevent its movement.

During manufacture, optical fiber 12 is inserted into and bonded within sheath 34. The silicone cladding 26 is then stripped from the end 28 of fiber 12 and end 28 is finely ground and highly polished to permit maximum transmission of light. Accordingly, because tip 28 can easily be damaged, it is necessary to provide a means for protecting it during assembly. Therefore, the proximal end 36 of sheath 34 is provided with a reduced outer diameter to receive a protective cap 38. Cap 38 is placed over end 36 during assembly to protect the polished end 28 of fiber 12 from damage.

With continued reference to FIG. 2, an outer sheath 48 is concentrically positioned over inner sheath 34. Sheath 48 is also generally cylindrical in shape, having diametrally reduced distal and proximal portions 50 and 52 respectively. In the preferred embodiment, outer sheath 48 is positioned over inner sheath 34 such that the distal end 49 of outer sheath 48 and the distal end 35 of inner sheath 34 are flush with each other. Sheaths 34 and 48 are secured in this position by set screw 56 which is threaded through bore 58 formed in approximately the center of outer sheath 48. In the preferred embodiment, sheath 48 is also made of brass because it is easy to machine to the high tolerances which are necessary to correctly align all of the parts. However, it is of course readily apparent that sheath 48 could also be made from stainless steel or any other suitable material which can be machined to close tolerances.

When assembled, concentric sheaths 34 and 48 are inserted into a stainless steel plug 62 which has a bore 64 extending through a portion of the length thereof. An annular shoulder 66 formed within plug 62 at the proximal end of bore 64 creates a section having a reduced diameter. Reduced proximal portion 52 of outer sheath 48 snugly fits within this reduced section of bore 64 formed by annular shoulder 66. When completely inserted, shoulder 68 of sheath 48 abuts against shoulder 66 and defines the farthest point to which sheath 48 can be inserted into plug 62. Sheath 48 is held in this fully inserted position by a spring 72 which is positioned over the diametrally reduced distal portion 50 of sheath 48 and is held in compression by a cap 96, as more fully discussed hereinafter.

With continued reference to FIG. 2, set screws 78 and 79 passing through threaded bores 82 and 83 in plug 62 support the distal end of sheath 48. Screws 78 and 79 are used to adjust the vertical alignment of sheath 48 within plug 62. By adjusting screws 78 and 79 to lower the distal end of sheath 48, the proximal end of sheath 48, and thus the tip 28 of fiber 12 which is bonded therein, is slightly raised. Accordingly, screws 78 and 79 act as a means for vertically adjusting the alignment of tip 28 of fiber 12. Since fiber 12 is typically only 100 microns in diameter (approximately the thickness of a human hair) the alignment adjustments which normally must be made are extremely small.

Figure 3:
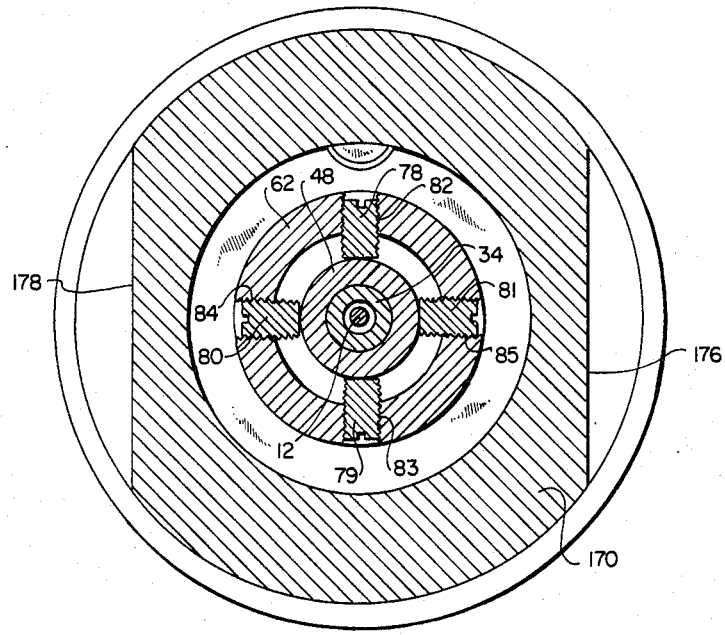
FIG. 3 is an enlarged cross-sectional view of the proximal connector taken along line 3—3 of FIG. 1.

Reference is next made to FIG. 3 which further illustrates the means by which the horizontal alignment of sheath 48 within plug 62 is adjusted. Screws 78 and 79 are again illustrated as being positioned to vertically adjust the alignment of sheath 48 within plug 62. Additional screws 80 and 81 are inserted through threaded bores 84 and 85 in plug 62 to horizontally adjust the alignment of sheath 48 within plug 62. Accordingly, by adjusting screws 78–81, the vertical and horizontal alignment of sheath 48 and thus, fiber 12, can be accomplished.

While reference has been made to vertical and horizontal adjustments with respect to screws 78–81, it will be appreciated that this is simply a convenient frame of reference used to describe any adjustments in two dimensions. It assumes that connector 16 is horizontally inserted into a side of the laser source. It is of course apparent that if connector 16 were to be inserted into the top of a laser source, the principles of alignment would be the same but the frame of reference would not be horizontal and vertical. Thus, as used herein, the terms "horizontal" and "vertical" are not intended to be limiting, but rather are simply used to denote adjustment along two essentially normal axes.

Referring again to FIG. 2, the proximal end 90 of plug 62 which extends beyond end 17 of connector 16 has an outer diameter which is slightly smaller than the rest of plug 62 and is sized to fit within a socket 91 formed in a laser source 94 which, in the preferred embodiment, may be an argon ion laser such as is manufactured by American Laser Corp. of Salt Lake City, Utah. The leading edge of end 90 is chamferred at 92 to facilitate insertion into socket 91 inasmuch as end 90 is machined to high tolerances to ensure a snug fit within socket 91. Thus, when plug 62 is inserted into socket 91, it is rigidly held in place such that the optical fiber 12 remains in alignment after adjustment.

The bore 65 which is formed in the proximal end 90 of plug 62 has a diameter larger than the outer diameter of inner sheath 34. A very small portion of the space between sheath 34 and end 90 of plug 62 is necessary to provide room for the end of sheath 34 to move horizontally and vertically as adjustments are made to align fiber 12. Additionally, after sheaths 34 and 48 have been inserted and secured within plug 62, tweezers, pliers, or another suitable instrument has to be inserted into bore 65 to remove cap 38 which protects tip 28 of fiber 12.

With continued reference to FIG. 2, the distal end 102 of plug 62 is threaded to receive a cylindrically shaped cap 96. The proximal end of cap 96 has a threaded bore 100 which mates with the threaded end 102 of plug 62. Section 102 of plug 62 is formed with a diameter slightly smaller than the diameter of the main body of plug 62, thus creating a shoulder 104. Face 106 of the proximal end of cap 96 abuts shoulder 104 when cap 96 is completely screwed onto plug 62.

Adjacent threaded bore 100 of cap 96 and coaxial therewith is a stepped bore 110. An end of spring 72 fits within stepped bore 110 and is held under compression between cap 96 and sheath 48 when cap 96 is completely screwed onto plug 62. Thus, spring 72 is biased so as to urge sheath 48 into plug 62 such that shoulder 68 of sheath 48 abuts annular shoulder 66 in plug 62 as previously described.

With continued reference to cap 96 as illustrated in FIG. 2, an enlarged bore 112 is formed in the distal end of cap 96. Bore 112 is in axial alignment with stepped bore 110 and is in communication therewith by means of bore 98 formed in the center of cap 96.

Bore 112 is designed to receive the proximal end of casing 14 which surrounds and protects optical fiber 12. Casing 14 is anchored within bore 112 by means of a ferrule 15 which is cemented onto the end of the casing 14, and which in turn is secured by set screws 156 and 158. In the preferred embodiment, screw 158 is rotated sixty degrees (60°) from the position illustrated and a third screw (not shown) is spaced 120° from screws 156 and 158. Thus, there are three screws equidistantly spaced around ferrule 15 to securely anchor it in place.

Ferrule 15 is generally conical in shape being tapered from its leading end 150 to its trailing end 152. The edge of leading end 150 is chamferred at 151 to facilitate insertion into bore 112 of cap 96. An annular groove 154 is formed around the circumference of ferrule 15 adjacent chamfer 151. Set screws 156 and 158 are inserted through threaded bores 160 and 162 in cap 96 and into groove 154 to anchor ferrule 15 within cap 96 after assembly.

Referring now to the proximal end of connector 16 as illustrated with continued reference to FIG. 2, collar 120 determines the depth to which plug 62 can be inserted into socket 91. It is important to be able to adjust the depth to which plug 62 can be inserted into the laser source to insure that tip 28 is positioned at the point of focus of the laser beam. Accordingly, cylindrical collar 120 circumferentially engages plug 62 behind proximal end 90. Collar 120 is releasably secured on plug 62 by set screw 122 which is located in threaded bore 124 in the bottom of collar 120. By loosening set screw 122, collar 120 is longitudinally adjustable along a portion of the length of plug 62.

Collar 120 has a cylindrical flange 126 which projects towards the proximal end of connector 16. Face 128 of flange 126 abuts against the face 129 of laser source 94 when plug 62 is completely inserted into socket 91. Thus, by adjusting collar 120 along the length of plug 62, the depth to which plug 62 will penetrate the socket 91 can be adjusted.

A bore 132 is formed in the upper portion of collar 120 into which pin 134 is inserted and held by means of a friction fit. Pin 134 mates with a bore 138 positioned immediately above the socket 91 in the laser source and the proximal end 136 of pin 134 is slightly rounded to facilitate insertion into bore 138. Accordingly, pin 134 acts as a reference point to insure that plug 62 can only be inserted into the laser source in one position and cannot thereafter be rotated, which rotation might cause optical fiber 12 to move out of alignment.

To protect the alignment adjustments after they have been made, an outer cap 170 is provided which covers connector 16 and shields all of the screws which are used to adjust the positioning of the optical fiber. Cap 170 is generally conical in shape and slides over the inner components of connector 16. The inner surface of proximal end 172 of cap 170 circumferentially engages collar 120 to seal end 17 of connector 16. On the distal end of cap 170, a lip 171 projects inwardly to engage ferrule 15 and seal the distal end of connector 16.

Cap 170 is secured in place by set screws 180 and 182 located in threaded bores 184 and 186 of cap 170. Screws 180 and 182 project into an annular groove 188 which is formed in cap 96.

In the preferred embodiment, cap 170 is formed from chrome plated brass for strength and appearance. However, other materials such as stainless steel or even some types of plastic would work equally well.

Figure 4:
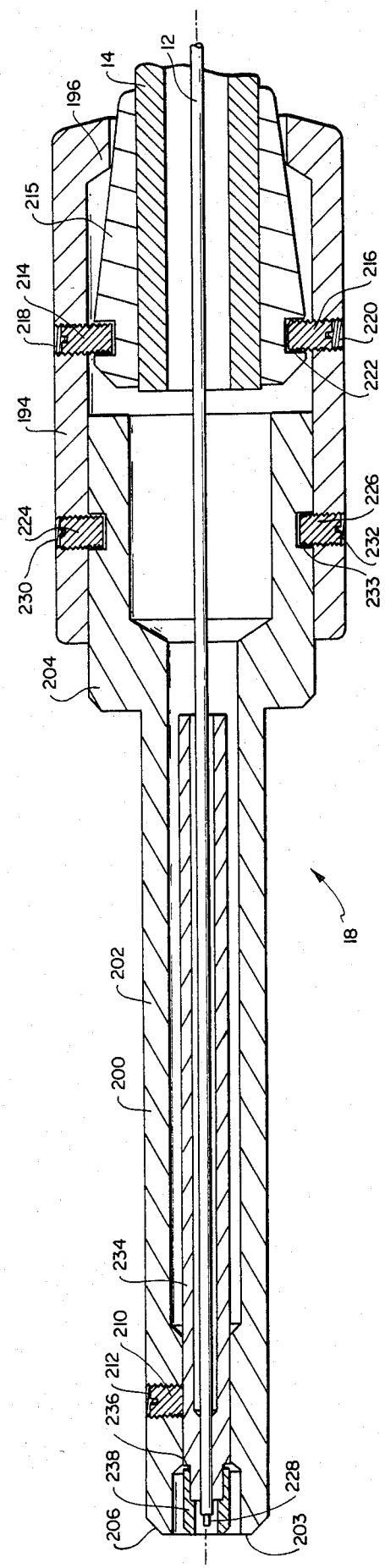
FIG. 4 is an enlarged cross-sectional view of the distal connector taken along line 4—4 of FIG. 1.

With reference now to FIG. 4, the component parts of distal connector 18 are illustrated. Fiber 12 passes axially through connector 18 and terminates in a sheath 234 which is identical in configuration to sheath 34 attached to the proximal end of fiber 12 located in connector 16. A cap 238 is positioned over reduced section 236 of sheath 234 to protect distal tip 228 of optical fiber 12 during assembly.

Sheath 234 is secured within a stainless steel plug 200 which is inserted into a socket (not shown) located in a surgical instrument such as a slit lamp or operating microscope. Plug 200 is generally cylindrical in shape having a distal section 202 and a radially enlarged proximal section 204. The leading edge of distal section 202 is chamferred at 206 to facilitate insertion of plug 200 into the socket in the surgical instrument.

During assembly, sheath 234 is inserted into plug 200 until the end of cap 238 is flush with the distal face 203 of plug 200. Set screw 210 located in threaded bore 212 is then used to secure sheath 234 in place.

With reference now to the proximal end of connector 18 illustrated in FIG. 4, a ferrule 215 is cemented to the distal end of casing 14 and is utilized to secure casing 14 within connector 18. Ferrule 215 is identical in configuration to ferrule 15 attached to the proximal end of casing 14.

A cap 194 forms the outer surface of connector 16 and serves to connect casing 14 with plug 200 as well as providing a means for grasping connector 18 for insertion or removal. Set screws 214 and 216 in threaded bores 218 and 220 are inserted into annular groove 222 formed in ferrule 215. In the preferred embodiment, set screw 216 and bore 220 are rotated sixty degrees (60°) from the position illustrated. A third bore and set screw (not shown) are provided and are spaced 120° from screws 214 and 126. Thus, these screws are equidistantly spaced around ferrule 215 to securely hold it in place.

Two additional set screws 224 and 226 located in threaded bores 230 and 232 are inserted into annular groove 233 formed in enlarged section 204 of plug 200. Cap 194 is also made of chrome plated brass in the preferred embodiment.

The proximal end of cap 194 has an inwardly projecting lip 196 which is designed to engage ferrule 215 when connector 18 is completely assembled. Lip 196 prevents debris from entering connector 18 and also provides additional support for securing ferrule 215 within connector 18.

Besides shielding fiber 12, casing 14 also serves as a tether to limit the distance which separates connectors 16 and 18. Accordingly, if the laser source and surgical instrument are separated to the entire length of assembly 10, the tension is absorbed by casing 14 and is not applied to fiber 12 which could cause the fiber to break.

As can be appreciated from the foregoing, the present invention provides a novel means for attaching an optical fiber to a laser source to transmit a laser beam to a surgical instrument such as a slit lamp or operating microscope. The invention provides a means whereby the optical fiber can easily be replaced should it break or become unuseable because of deterioration. Thus, many of the problems associated with the prior art systems are eliminated. There is no need to return the laser source to the factory for repairs if the fiber is damaged. Additionally, the cost of maintaining replacement fibers is much less than the cost of maintaining a back-up laser system.

In use, assembly 10 is removed from its packaging and cap 38 which protects tip 28 of fiber 12 is carefully removed from the proximal end of connector 16. Care must be taken during and after removal of cap 38 to insure that tip 28 of fiber 12 is not damaged.

Pin 134 and plug 62 of connector 16 are then aligned with their corresponding sockets 138 and 91 in the laser source and are inserted therein. It is important to insure that plug 62 is inserted completely each time so that its positioning is consistent.

Once connector 16 is in place, screws 180 and 182 which secure cap 170 in place are loosened. Cap 170 can then be slid back onto casing 14 to reveal the adjusting mechanisms within connector 16.

If the depth of optical fiber 12 within the laser source is not correct such that tip 28 is at the point of focus of the laser beam, set screw 122 is loosened and plug 62 is longitudinally adjusted within collar 120. After adjustment, screw 122 is again tightened to secure plug 62 in place.

Adjustments are then made to the horizontal and vertical alignment of fiber 12. With cap 170 removed, screws 78-81 in plug 62 are exposed. (See FIG. 3.) If the tip 28 of fiber 12 is too high, screw 79 is loosened slightly and then screw 78 is tightened, thus lowering the portion of sheath 48 which is supported by screws 78-81. Since sheath 48 pivots ever so slightly about the point where it passes through annular ridge 66, (see FIG. 2) the movement of the distal end of sheath 48 in one direction causes the proximal end of sheath 48, and thus tip 28 of fiber 12, to move in the opposite direction.

Similar adjustments can be made with screws 80 and 81 to horizontally align fiber 12 with the laser beam. Because fiber 12 is extremely thin, the adjustments which are usually necessary to precisely align it with the laser beam are extremely small.

After all of the adjustments are complete, cap 170 is slid back onto connector 16 and screw 180 and 182 are tightened to secure it in place.

Once connector 16 has been adjusted to align fiber 12 with the laser beam, assembly 10 can be disconnected from the laser source without disturbing the adjustments. Thus, assembly 10 can be removed for storage between uses. Additionally, should optical fiber 12 deteriorate or become broken, assembly 10 can easily be disconnected and replaced with a different assembly.

It should further be appreciated that while the present invention has been particularly described with reference to the presently preferred embodiment, the invention may be embodied in other specific forms without departing from its spirit or essential characteristics. Thus, the described embodiment is to be considered in all respects only as illustrative and not restrictive. The scope of the invention is, therefore, indicated by the appended claims rather than by the foregoing description, and all modifications or changes which come within the meaning and range of equivalency of the claims are to be embraced within their scope.

What is claimed and desired to be secured by United States Letters Patent is:

1. In a laser system, in combination:
(a) laser apparatus having:
   (i) a cylindrical laser beam connector receptacle for receiving a cylindrical connector plug forming part of the proximal end of a detachable optical fiber assembly connecting said laser apparatus to a laser instrument;
   (ii) a flat surface surrounding the entrance to said connector receptacle;
   (iii) means providing a laser beam source positioned on the axis of said connector receptacle; and
   (iv) offset from said laser beam connector receptacle a cylindrical guide pin receptacle with an entrance surrounded by said flat surface and concentric with an axis parallel to the axis of said laser beam connector receptacle;
(b) a laser instrument operative with said laser beam and having a cylindrical instrument receptacle for receiving a cylindrical connector plug forming part of the distal end of a detachable optical fiber assembly connecting said laser apparatus and instrument;

(c) an elongated flexible optical fiber structure comprising:
  (i) a central optical fiber core for transmitting said beam;
  (ii) optical transmission enhancement cladding covering said fiber core;
  (iii) a tubular fiber core protective sheath loosely surrounding said core and cladding for a major portion of the length thereof, said protective sheath terminating inwardly from each of the respective proximal and distal ends of said core and cladding, said core being relatively fragile with respect to the fragility of said core protective sheath; and
  (iv) a ferrule surrounding and secured to said protective sheath at each of the respective proximal and distal ends thereof enabling stress applied to said ferrules and thus to said protective sheath to be isolated from the more fragile said optical fiber core;
(d) a proximal connector assembly mated to said laser apparatus connector and pin receptacles for connecting the proximal end of said optical fiber structure to said laser apparatus, comprising:
  (i) a first tubular substantially rigid sheath having a first concentric bore extending from its distal end for a major portion of its length and a second concentric bore of reduced diameter at its proximal end, a proximal end portion of said optical fiber core and cladding located outwardly from the proximal end of said fiber core protective sheath being loosely confined in said first bore and fixedly concentrically secured in said second bore with the extreme proximal end of said fiber core extending beyond the proximal end of said first sheath;
  (ii) a second substantially rigid tubular sheath concentrically mounted on said first said tubular sheath and extending from the distal end of said first sheath for a major portion of the length of said first sheath, said second sheath being secured to said first sheath for adjustable lengthwise positioning thereon;
  (iii) a third substantially rigid tubular sheath having enlarged concentric bores formed at the proximal and distal ends thereof and therebetween a concentric connecting bore of reduced size defined by an internally-formed annular shoulder, said second tubular sheath having its proximal end seated in said shoulder and being mounted within the enlarged distal end bore of said third sheath to allow vertical and horizontal positioning therein, the proximal end of said first sheath extending in a proximal direction from said shoulder being mounted within the enlarged proximal end bore of said third sheath to allow vertical and horizontal positioning therein, said third tubular sheath at its proximal end being precision formed to mate and snugly fit within said laser apparatus receptacle and thereby locate the extreme proximal end of said optical fiber core proximate said laser beam source;
  (iv) a fourth tubular sheath threadably secured at its proximal end to a mated distal end of said third tubular sheath, having an enlarged bore at its distal end and a connecting bore of reduced diameter formed by an internally-formed annular shoulder, said ferrule at the proximal end of said optical fiber structure protective sheath being releasably secured within the said enlarged bore at the distal end of said fourth sheath;
  (v) a compression spring seated between said fourth sheath annular shoulder and the distal end of said second tubular sheath and operative to resiliently force the proximal end of said second tubular sheath into a seated position in said third tubular sheath annular shoulder while permitting at least limited vertical and horizontal positioning of the distal end of said second sheath within the enlarged bore within the distal end of said third sheath;
  (vi) a plurality of set screws mounted in spaced circumferential positions in said third tubular sheath and adjustably positioned in contact with the outer surface of a distal end portion of said second tubular sheath, selected ones of said set screws being adjustable to tilt said second sheath both vertically and horizontally on said third tubular sheath annular shoulder to precisely align the extreme proximal end of said optical fiber with said laser apparatus source;
  (vii) a collar concentric with and adjustably mounted for lengthwise positioning on said third tubular sheath and having a proximal end portion thereof engagable with said laser apparatus flat surface to control the depth of insertion of said third sheath proximal end in said laser apparatus receptacle;
  (viii) a guide pin secured in said collar and located on an offset axis parallel to the axis of said collar and being adapted to fit into said guide pin receptacle for aligning the proximal end of said third sheath with said laser apparatus receptacle; and
  (ix) a cover surrounding said collar, third and fourth tubular sheaths and removably secured to said fourth tubular sheath; and
(e) a distal connector assembly for connecting the distal end of said optical fiber structure to said laser instrument, comprising:
  (i) a fifth tubular substantially rigid sheath having a first concentric bore extending from its proximal end for a major portion of its length and a second concentric bore of reduced diameter at its distal end, a distal end portion of said optical fiber core and cladding located outwardly from the distal end of said fiber core protective sheath being loosely confined in said fifth sheath first bore and fixedly concentrically secured in said fifth sheath second bore with the extreme distal end of said fiber core extending beyond the distal end of said fifth sheath;
  (ii) a sixth substantially rigid tubular sheath having a first concentric bore at the outer distal end thereof surrounding the distal end of said fifth sheath and the distal end of said fiber core, a second concentric bore extending for a major portion of the length thereof and a third concentric bore formed by an internally-formed annular shoulder and communicating said sixth sheath first and second bores, a distal outer end portion of said sixth sheath being adapted to mate and fit in said laser instrument receptacle and having a larger proximal end portion;
  (iii) a cover having its distal end releasably secured to said sixth sheath larger proximal end portion; and
  (iv) means securing the other of said ferrules at the distal end of said optical fiber structure in a manner enabling force transmitted thereto to be transferred to said sixth sheath.

* * * * *